(12) United States Patent
Mantripragada et al.

(10) Patent No.: US 7,847,112 B2
(45) Date of Patent: Dec. 7, 2010

(54) POLYMORPHS OF ATOVAQUONE AND PROCESS OF PREPARATION THEREOF

(75) Inventors: Narayana Rao Mantripragada, New Panvel (IN); Dhananjay Govind Sathe, Thane (IN); Venkatasubramanian Radhakrishnan Tarur, Mumbai (IN); Kamlesh Digambar Sawant, Mumbai (IN); Gautam Ramjibhai Patel, Rajkot (IN)

(73) Assignee: Health Science Funding, LLC, Morristown, NJ (US)

( * ) Notice: Subject to any disclaimer, the term of this patent is extended or adjusted under 35 U.S.C. 154(b) by 1153 days.

(21) Appl. No.: 10/569,036

(22) PCT Filed: Jul. 16, 2004

(86) PCT No.: PCT/IN2004/000213

§ 371 (c)(1),
(2), (4) Date: Feb. 18, 2006

(87) PCT Pub. No.: WO2006/008752

PCT Pub. Date: Jan. 26, 2006

(65) Prior Publication Data

US 2006/0241311 A1   Oct. 26, 2006

(51) Int. Cl.
*C07C 50/00* (2006.01)
*A61K 31/12* (2006.01)
*A01N 35/00* (2006.01)

(52) U.S. Cl. .......................... 552/296; 552/299; 514/682
(58) Field of Classification Search ................. 552/296, 552/299; 514/682
See application file for complete search history.

(56) References Cited

U.S. PATENT DOCUMENTS

| 2,553,647 A | 5/1951 | Fieser et al. |
| 4,981,874 A | 1/1991 | Latter et al. |
| 5,856,362 A * | 1/1999 | Hudson ...................... 514/682 |

FOREIGN PATENT DOCUMENTS

EP         0123238       * 10/1984

OTHER PUBLICATIONS

Louis F. Fieser, et al, Napthoquinone Antimalarials. IV-XI. Synthesis, 70 J. Am. Chem. Soc. 3174, 3188-91 (1948).*

* cited by examiner

*Primary Examiner*—Frederick Krass
*Assistant Examiner*—Sean Basquill
(74) *Attorney, Agent, or Firm*—Pharmaceutical Patent Attorneys, LLC

(57) ABSTRACT

Novel crystalline forms of anti *Pneumocystis carinii* compound (2-[4-(4-Chlorophenyl)cyclohexyl]-3-hydroxy-1,4-naphthoquinone) commonly known as Atovaquone and methods for producing the same is disclosed herein. This also provides pharmaceutical compositions comprising the said polymorphs of Atovaquone and method of treating *Pneumocystis carinii* pneumonia, the method comprising administering to a warm blooded animal an effective amount of a product-by-process composition of matter comprising polymorphic forms of Atovaquone.

28 Claims, 6 Drawing Sheets

POLYMORPHS OF ATOVAQUONE AND PROCESS OF PREPARATION THEREOF

This application is the United States national stage entry of, and claims priority from, PCT application Serial No. PCT/IN2004/000213, filed 16 Jul. 2004, the contents of which are hereby incorporated by reference.

TECHNICAL FIELD

The present invention relates to novel crystalline forms of anti *Pneumocystis carinii* compound (2-[4-(4-Chlorophenyl) cyclohexyl]-3-hydroxy-1,4-naphthoquinone) commonly known as Atovaquone and methods for producing the same.

BACKGROUND AND PRIOR ART

*Pneumocystis carinii* is a parasite, which has a natural habitat in lung tissue, in a host with normal immune system. Without treatment *Pneumocystis carinii* pneumonia is almost always fatal in immuncompromised host. U.S. Pat. No. 4,981,874 discloses the process of preparation and the activity of the Atovaquone.

Polymorphs of Atovaquone are not reported yet. The term 'polymorphs', is meant to include different physical forms, crystalline/liquid crystalline/amorphous forms.

Polymorphic studies have become very interesting and important as many active pharmaceutical ingredients exhibit polymorphism and some/one of the polymorphic form exhibit high bio-availability and also much better activity as compared to other polymorphs.

We have focused our research to develop new polymorphic forms with an object to develop novel polymorphic forms of anti *Pneumocystis carinii* compound Atovaquone.

SUMMARY OF THE INVENTION

U.S. Pat. No. 4,981,874 discloses the recrystallization/purification of Atovaquone using solvent acetonitrile. The polymorphic form obtained by this method is referred hereafter as Form I, characterized by an X-ray powder diffraction pattern having peaks at about 7.2, 11.04, 11.77, 19.34, 21.14, 24.61, 25.28, 28.4±0.2 degrees. The DSC thermogram of Form I shows a small endotherm at 197° C. followed by a sharp endotherm at 222° C.

The present invention provides crystalline Atovaquone Form II, characterized by an X-ray powder diffraction pattern having peaks at about 7.02, 9.68, 10.68, 11.70, 14.25, 14.83, 18.60, 19.29, 23.32, 24.54±0.2 degrees. The DSC thermogram of Form II shows a small endotherm at 169° C. followed by a sharp endotherm at 222° C.

The present invention also provides crystalline Atovaquone Form III, characterized by an X-ray powder diffraction pattern having peaks at about 6.99, 9.65, 12.67, 20.07, 20.65, 20.99, 21.88, 22.10, 25.56±0.2 degrees. The DSC thermogram of Form III shows characteristic sharp endotherm at 222° C.

The present invention also provides a process for preparing Form I comprising of dissolution of crude Atovaquone in a solvent; adding anti-solvent to the solution, cooling the resultant solution and, collecting the crystals of Form I.

The present invention also provides a process for converting crystalline Atovaquone Form I to Form II, comprising dissolution of Atovaquone Form I in a solvent by heating; cooling the resultant solution and, collecting the crystals of Form II.

The present invention also provides a process for converting crystalline Atovaquone Form I to Form III, comprising dissolution of Atovaquone Form I in a solvent by heating; cooling the resultant solution and, collecting the crystals of Form III.

The present invention also provides a process for preparing crystalline Atovaquone Form III, comprising dissolution of Atovaquone Form I in a solvent; adding anti-solvent to the solution, cooling the resultant solution and, collecting the crystals of Form III.

Pharmaceutical compositions comprising therapeutically effective amount of polymorphs II and III of Atovaquone are also disclosed herein.

A method of treating *Pneumocystis carinii* pneumonia, the method comprising administering to a warm blooded animal an effective amount of a product-by-process composition of matter comprising polymorphic forms of Atovaquone is also envisaged as part of this invention.

DESCRIPTION OF THE INVENTION

The present invention provides new crystal forms of Atovaquone. The discovery of new crystalline form of Active pharmaceutical ingredient will be advantageous with regard to improvement in performance of the product.

The present invention also relates to the solid-state forms (i.e. Polymorphs) of Atovaquone that can be prepared by the methods described herein.

As used herein, a solvent is any liquid substance which has capacity to dissolve the organic compound Atovaquone, either at room temperature or higher. Antisolvent is an organic solvent in which organic compound such as Atovaquone has poor solubility.

As used herein, room temperature means a temperature from about 25° C. to 30° C.

X-ray powder diffraction pattern has been obtained on D8-Advance, Broker AXE, Germany, diffractometer equipped with scintillation detector using Copper Kα ($\lambda$=1.5406 A) radiation with scanning range between 2-50 η at scanning speed of 2°/min.

Differential Scanning Calorimeter was performed on Mettler DSC 20 instrument. Samples of 2 mg to 3 mg weighed in aluminum crucible with holes were scanned at a heating rate of 10° C. per minute under Nitrogen atmosphere at a rate of 35 ml/min.

Atovaquone Form I

Atovaquone is prepared by the method described in U.S. Pat. No. 4,981,874 which is referred as Form I. The X-ray powder diffraction diagram and DSC thermograms of Form I are shown in FIGS. 1 and 4 respectively.

Preparation of Atovaquone Form I

Example 1

Ig. of crude Atovaquone Form I was dissolved in 10 mJL methylene dichloride at room temperature. To this solution 20 mL of methanol was added drop wise under stirring at same temperature. The slurry obtained was stirred for 4 hrs. at the same temperature. The solid was filtered and dried to get Form I.

Example 2

Ig. of crude Atovaquone Form I was dissolved in 10 mL methylene dichloride at room temperature. To this solution 20 mL of n-Heptane was added drop wise under stirring at same temperature. The slurry obtained was stirred for 4 hrs. at the same temperature. The solid was filtered and dried to get Form I.

Preparation of Atovaquone Form II

Atovaquone Form II is prepared from Form I by the method described below and the DSC thermogram, X-ray powder diffraction diagram of Form II are shown in FIGS. 2 and 5 respectively

Example 3

1g. of Atovaquone Form I was dissolved in 5 niL 1,4-Dioxane under reflux condition. The clear solution was allowed to cool to room temperature for 30 minutes and then cooled at 5° C. for 4 hours. The solid obtained was then recovered on Buchner funnel and dried to get Form II.

Preparation of Atovaquone Form III

Atovaquone Form III is prepared from Form I by the method described below and the DSC thermogram, X-ray powder diffraction diagram of Form III are shown in FIGS. 3 and 6 respectively

Example 4

0.5 g Atovaquone Form I was dissolved in 20 niL Acetone under reflux condition. 40 ml of water was maintained at 0° C. and to this cold water, the hot solution of the Atovaquone was added dropwise with stirring. The solution was maintained at the same temperature for 1 hr. The solid thus obtained was filtered and dried to get Form III.

Example 5

0.5 g. Atovaquone Form I was dissolved in 15 niL chloroform at room temperature. To this solution 20 mL of methanol was added drop wise under stirring at same temperature. The slurry obtained was stirred for 4 hrs. at the same temperature. The solid was filtered and dried to get Form III.

Example 6

0.5 g. Atovaquone Form I was dissolved in 80 mL diisopropyl ether under reflux condition. The solution was cooled to room temperature and maintained at same temperature for 4 hrs. The solid was filtered and dried to get Form III.

Figure 1:
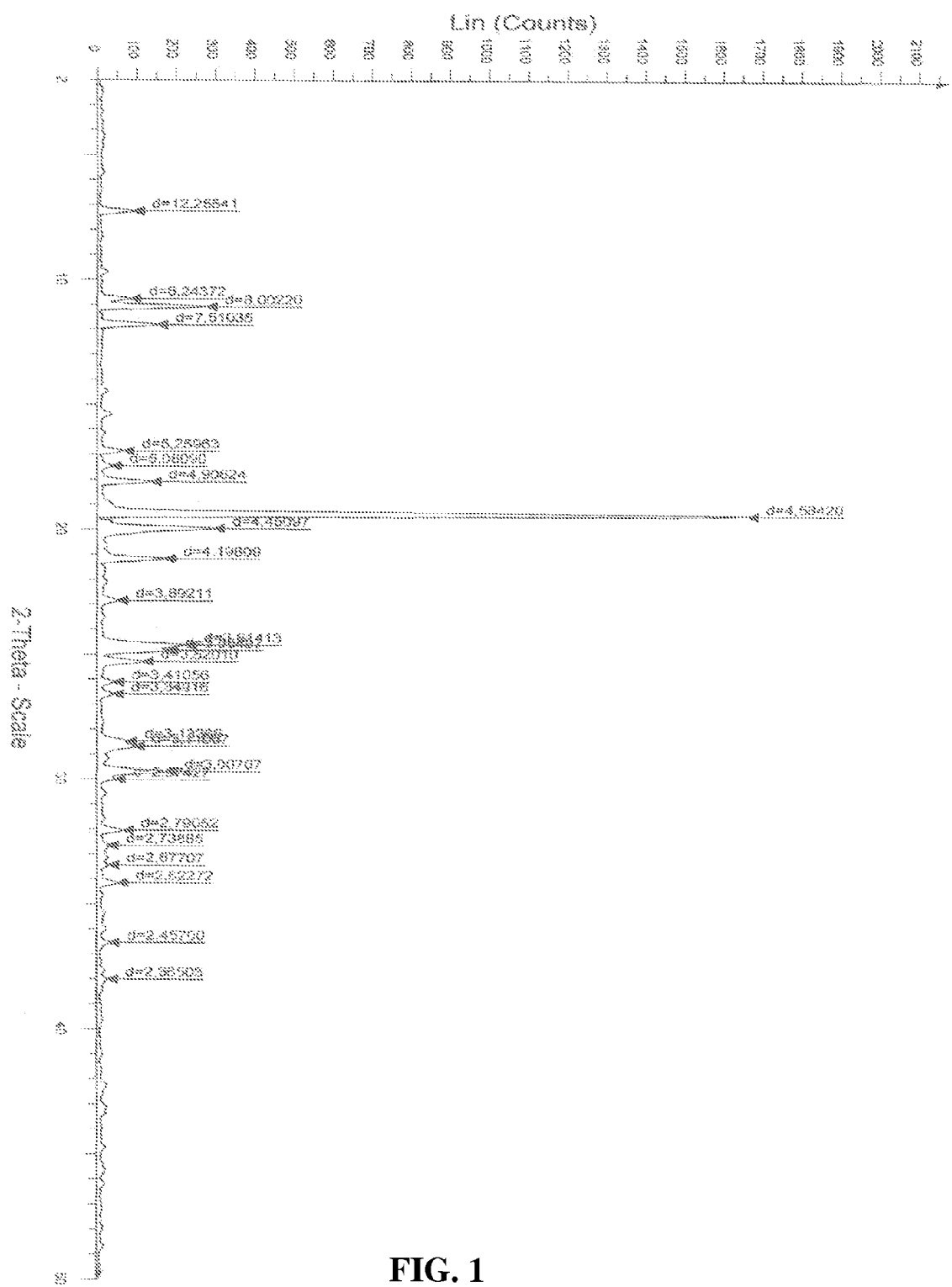
FIG. 1 Shows the X-ray Diffraction Diagram of Atovaquone Form I
Figure 4:
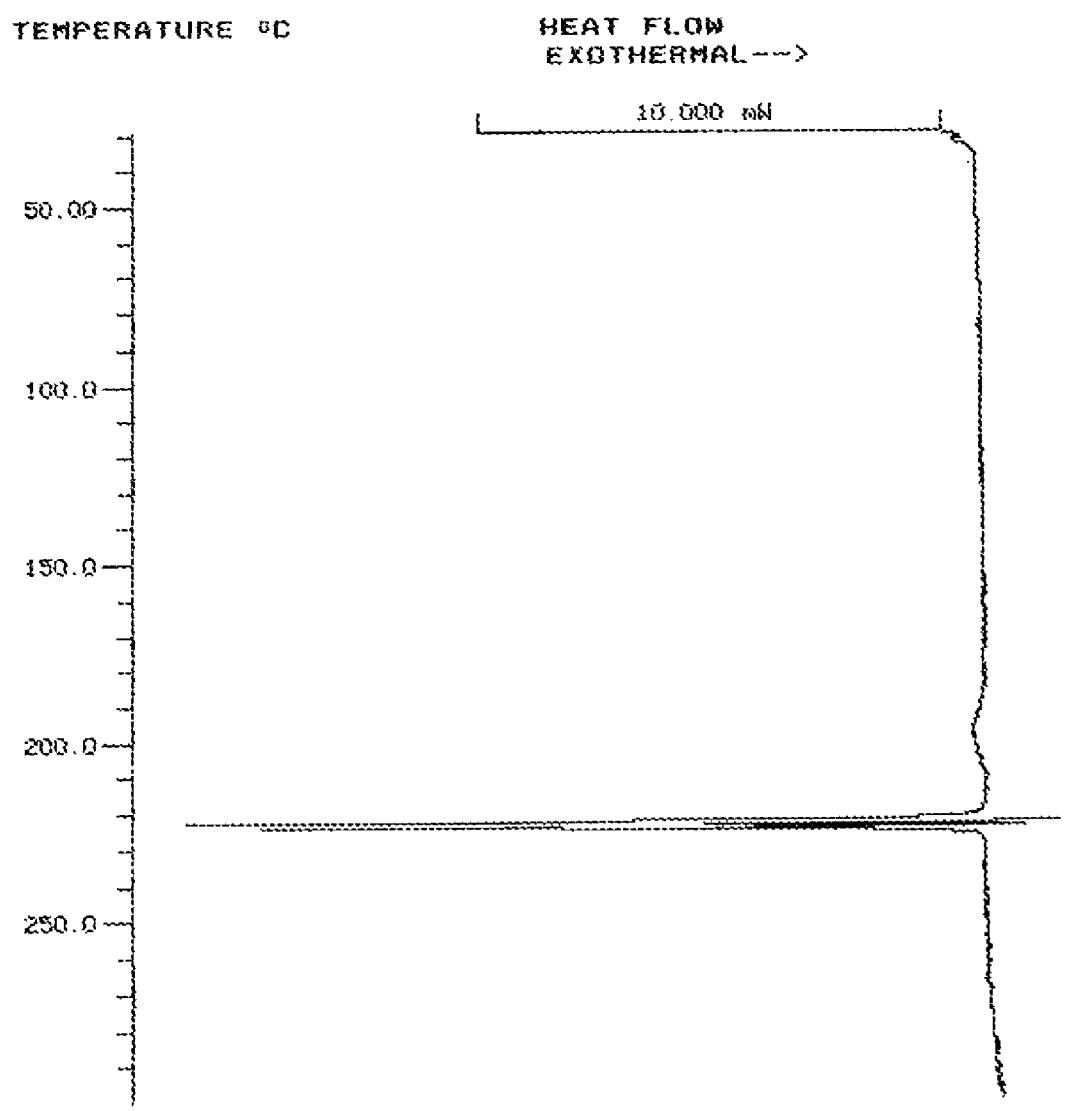
FIG. 4 Shows the DSC Thermogram of Atovaquone Form I

The polymorphic form I obtained by this method is characterized by an X-ray powder diffraction pattern (FIG. 1) having peaks at about 7.2, 11.04, 11.77, 19.34, 21.14, 24.61, 25.28, 28.4±0.2 degrees. The DSC thermogram of Form I (FIG. 4) shows a small endotherm at 197° C. followed by a sharp endotherm at 222° C.

Figure 2:
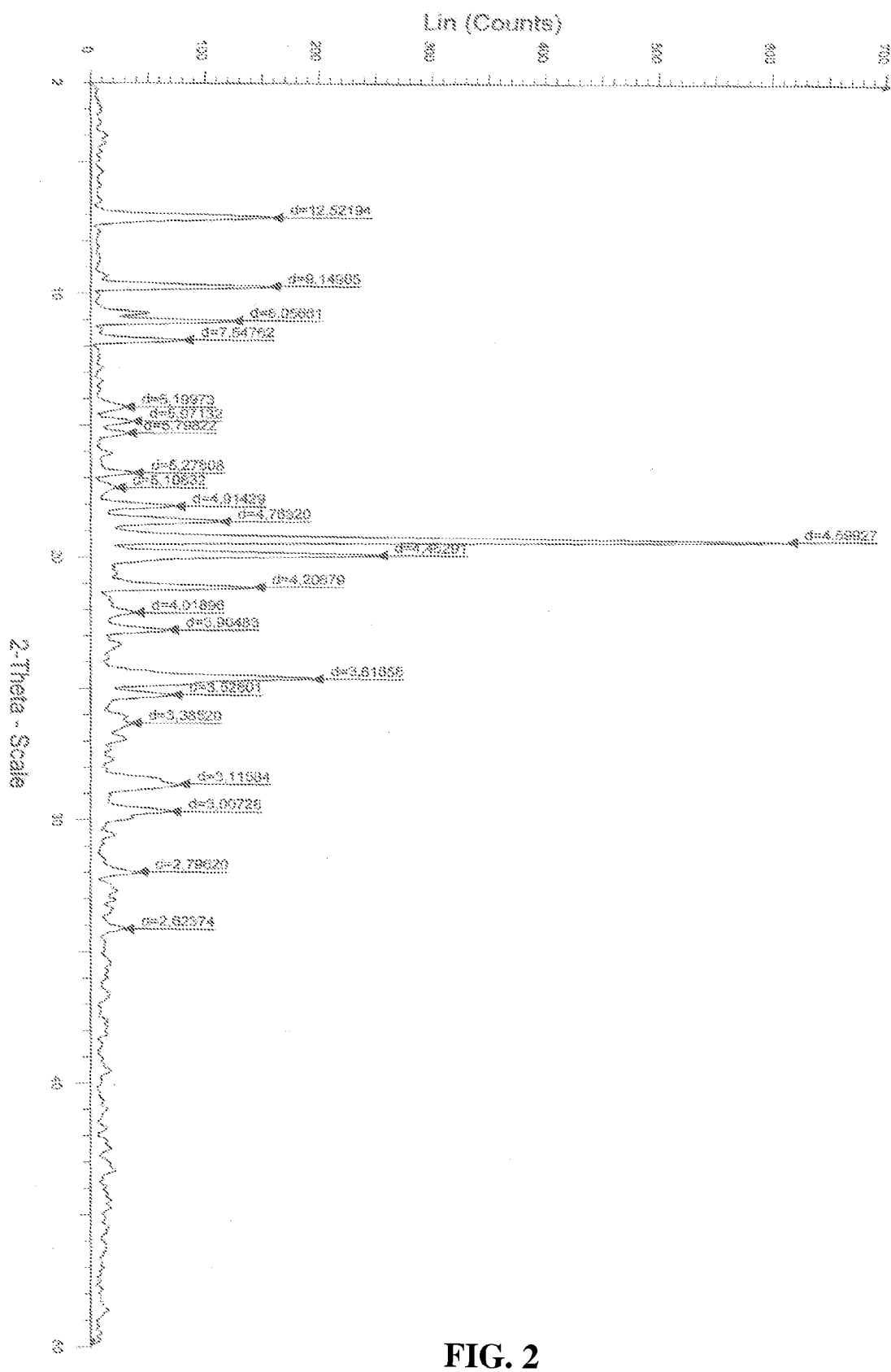
FIG. 2 Shows the X-ray Diffraction Diagram of Atovaquone Form II
Figure 3:
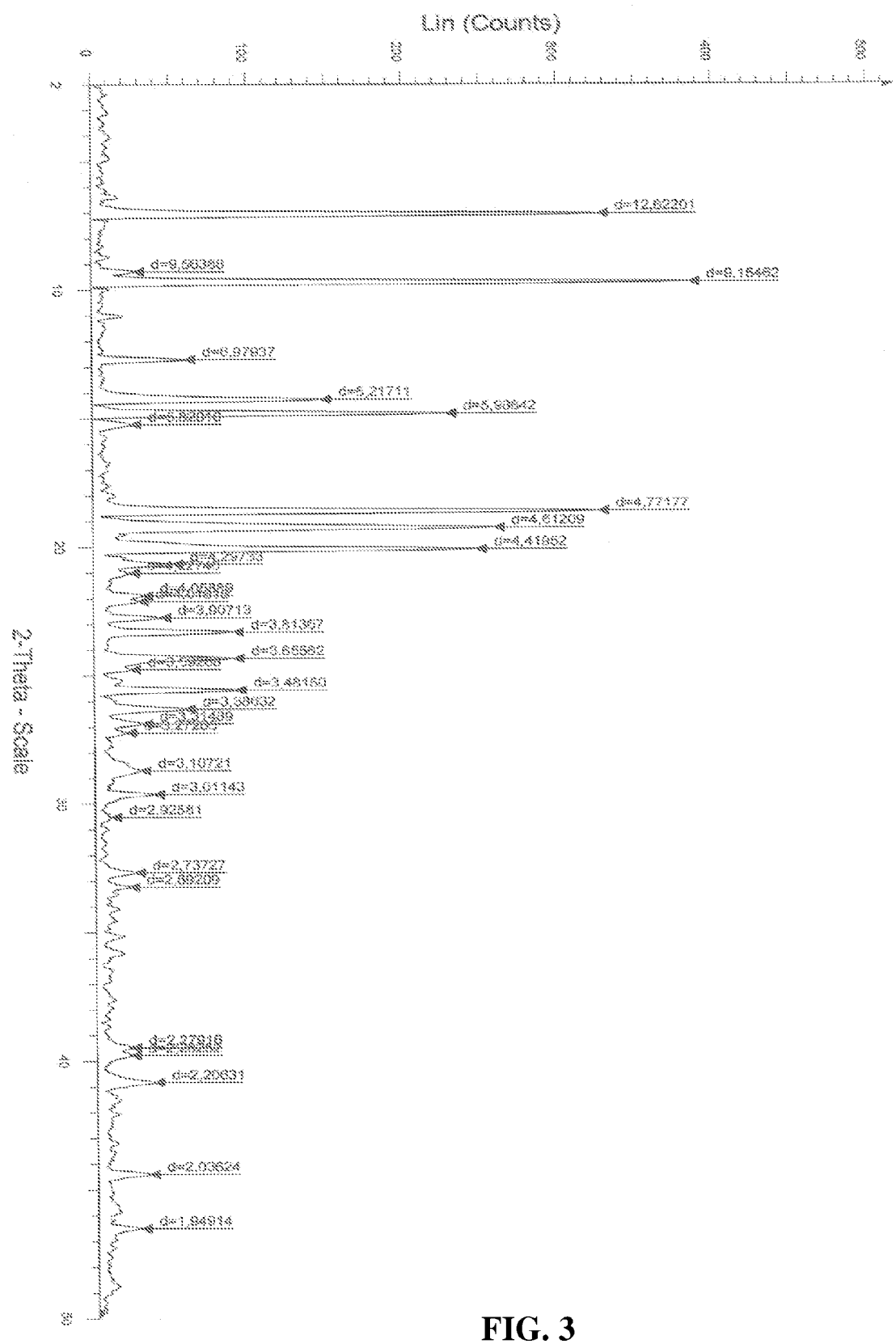
FIG. 3 Shows the X-ray Diffraction Diagram of Atovaquone Form III
Figure 5:
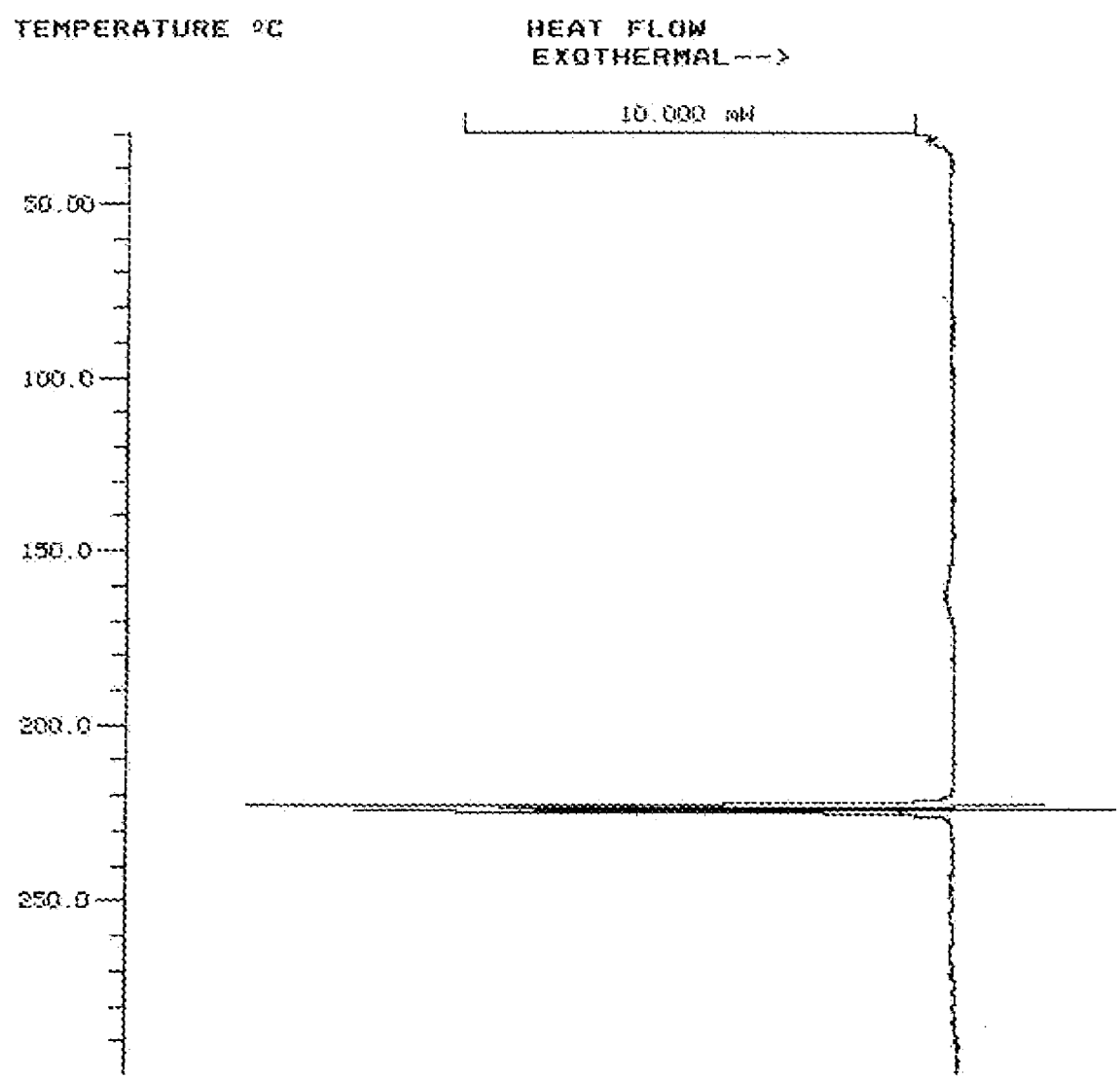
FIG. 5 Shows the DSC Thermogram of Atovaquone Form II

The present invention provides crystalline Atovaquone Form II, characterized by an X-ray powder diffraction pattern having peaks at about 7.02, 9.68, 10.68, 11.70, 14.25, 14.83, 18.60, 19.29, 23.32, 24.54±0.2 degrees as shown in FIG. 2. The DSC thermogram of Form II in FIG. 5 shows a small endotherm at 169° C. followed by a sharp endotherm at 222° C.

Figure 6:
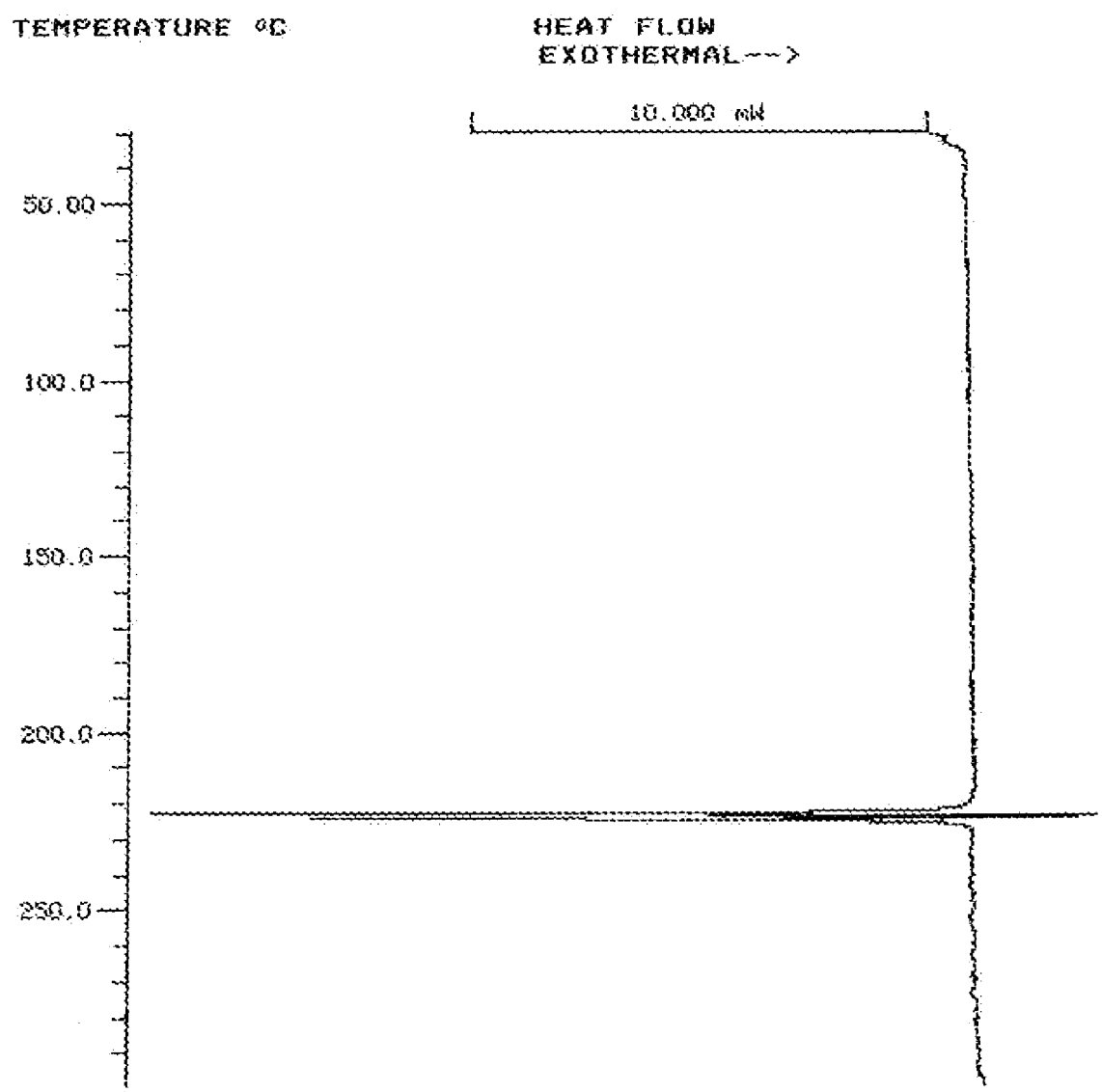
FIG. 6 Shows the DSC Thermogram of Atovaquone Form III

The present invention also provides crystalline Atovaquone Form III, characterized by an X-ray powder diffraction pattern (FIG. 4) having peaks at about 6.99, 9.65, 12.67, 20.07, 20.65, 20.99, 21.88, 22.10, 25.56±0.2 degrees. The DSC thermogram of Form III (FIG. 6) shows characteristic sharp endotherm at 222° C.

Pharmaceutical compositions comprising therapeutically effective amount of polymorphs II and III of Atovaquone are prepared by conventional methods.

A method of treating *Pneumocystis carinii* pneumonia, the method comprising administering to a warm blooded animal an effective amount of a product-by-process composition of matter comprising polymorphic forms of Atovaquone is also envisaged as part of this invention

We claim:

1. A crystalline Atovaquone characterized by X-ray diffraction peaks at 2θ values of about 7.02, 9.68, 10.68, 11.70, 14.83, 18.60, 19.29, 23.32 and 24.54.

2. The crystalline Atovaquone as claimed in claim 1 exhibiting a DSC thermogram that has an endotherm at about 169° C.

3. A process for making crystalline Atovaquone of claim 1 comprising the steps of: a.) dissolving Atovaquone Form 1 in 1,4-Dioxane at reflux temperature of the solvent to form a solution; b.) cooling the solution at about 5° C. to precipitate Atovaquone crystals; c.) collecting the precipitated crystals and; d.) drying the crystals.

4. A crystalline Atovaquone having X ray diffraction peaks at 2θ values of about 6.99, 9.65, 12.67, 14.98, 19.40, 20.07, 20.65, 20.99, 21.88, 22.10 and 25.56.

5. The crystalline Atovaquone as claimed in claim 4 exhibiting a DSC thermogram that has a characteristic endotherm at about 222° C., said DSC thermogram having no significant peak at about 197° C.

6. A process for making crystalline Atovaquone as claimed in claim 4 comprising the steps of either: a.) dissolving Atovaquone Form 1 in diisopropyl ether at reflux temperature of the solvent to form a solution; b.) cooling the solution at room temperature to precipitate Atovaquone crystals; c.) collecting the precipitated crystals and d.) drying the crystals Or 1.) dissolving Atovaquone Form 1 in a solvent selected from the groups consisting of a chlorinated solvent or ketone at reflux temperature of the solvent to form a solution, then adding an anti-solvent selected from the group consisting of methanol, ethanol, isopropanol, and water until turbidity of the solution is achieved; 2.) cooling the solution to precipitate Atovaquone crystals; 3.) collecting the precipitated crystals and 4.) drying the crystals.

7. Crystalline Atovaquone Form II or crystalline Atovaquone Form III either alone or in combination with polymorphic form I for the formulation of medicament for the treatment of *Pneumocystis carinii* pneumonia infections.

8. The crystalline Atovaquone of claim 1, having a d90 value of greater than 3 microns.

9. The crystalline Atovaquone of claim 8, having a d90 value of between about 4 and about 15 microns.

10. The crystalline Atovaquone of claim 9, having a d90 value of greater than about 5 microns.

11. The crystalline Atovaquone of claim 10, having a d90 value of greater than about 6 microns.

12. The crystalline Atovaquone of claim 4, having a d90 value of greater than 3 microns.

13. The crystalline Atovaquone of claim 12, having a d90 value of between about 4 and about 15 microns.

14. The crystalline Atovaquone of claim 13, having a d90 value of greater than about 5 microns.

15. The crystalline Atovaquone of claim 14, having a d90 value of greater than about 6 microns.

16. The crystalline Atovaquone of claim 4, said X-ray diffraction peak comprising an X-ray diffraction peak with a 2 Theta value of about 6.99.

17. The crystalline Atovaquone of claim 4, said X-ray diffraction peak comprising an X-ray diffraction peak with a 2 Theta value of about 9.65.

18. The crystalline Atovaquone of claim 4, said X-ray diffraction peak comprising an X-ray diffraction peak with a 2 Theta value of about 12.67.

19. The crystalline Atovaquone of claim 4, said X-ray diffraction peak comprising an X-ray diffraction peak with a 2 Theta value of about 14.98.

20. The crystalline Atovaquone of claim 4, said X-ray diffraction peak comprising an X-ray diffraction peak with a 2 Theta value of about 19.40.

21. The crystalline Atovaquone of claim 4, said X-ray diffraction peak comprising an X-ray diffraction peak with a 2 Theta value of about 20.07.

22. The crystalline Atovaquone of claim 4, said X-ray diffraction peak comprising an X-ray diffraction peak with a 2 Theta value of about 20.65.

23. The crystalline Atovaquone of claim 4, said X-ray diffraction peak comprising an X-ray diffraction peak with a 2 Theta value of about 20.99.

24. The crystalline Atovaquone of claim 4, said X-ray diffraction peak comprising an X-ray diffraction peak with a 2 Theta value of about 21.88.

25. The crystalline Atovaquone of claim 4, said X-ray diffraction peak comprising an X-ray diffraction peak with a 2 Theta value of about 22.10.

26. The crystalline Atovaquone of claim 4, said X-ray diffraction peak comprising an X-ray diffraction peak with a 2 Theta value of about 25.56.

27. A pharmaceutical finished dosage form, said finished dosage form comprising atovaquone active pharmaceutical ingredient, said atovaquone active pharmaceutical ingredient having the X-ray diffraction peaks as claimed in claim 1, said atovaquone active pharmaceutical ingredient in particles having a d90 value of greater than 3 microns and a d90 value of less than about 15 microns.

28. A pharmaceutical finished dosage form, said finished dosage form comprising atovaquone active pharmaceutical ingredient, said atovaquone active pharmaceutical ingredient having the X-ray diffraction peaks as claimed in claim 4, said atovaquone active pharmaceutical ingredient in particles having a d90 value of greater than 3 microns and a d90 value of less than about 15 microns.

\* \* \* \* \*